United States Patent [19]
Wulfman

[11] Patent Number: 5,766,190
[45] Date of Patent: Jun. 16, 1998

[54] CONNECTABLE DRIVESHAFT SYSTEM

[75] Inventor: Edward I. Wulfman, Woodinville, Wash.

[73] Assignee: Boston Scientific Corporation Northwest Technology Center, Inc., Redmond, Wash.

[21] Appl. No.: 449,555

[22] Filed: May 24, 1995

[51] Int. Cl.$^6$ .................................................. A61B 17/22
[52] U.S. Cl. ............................................... 606/159; 606/180
[58] Field of Search ................................... 606/159, 170, 606/180, 79, 167, 171, 173; 604/22, 53, 49

[56] References Cited

U.S. PATENT DOCUMENTS

| | | |
|---|---|---|
| 3,309,772 | 3/1967 | Lieb et al. . |
| 3,809,093 | 5/1974 | Abraham . |
| 3,892,117 | 7/1975 | Nelson . |
| 3,937,222 | 2/1976 | Banko . |
| 4,264,307 | 4/1981 | Neuwirth . |
| 4,445,509 | 5/1984 | Auth ............................ 128/751 |
| 4,591,355 | 5/1986 | Hilse ........................... 604/159 |
| 4,646,736 | 3/1987 | Auth ............................ 128/303 |
| 4,679,557 | 7/1987 | Opie et al. .................. 128/305 |
| 4,728,319 | 3/1988 | Masch .......................... 604/22 |
| 4,729,763 | 3/1988 | Henrie . |
| 4,747,406 | 5/1988 | Nash ............................ 128/305 |
| 4,771,774 | 9/1988 | Simpson et al. ............ 128/305 |
| 4,792,327 | 12/1988 | Swartz .......................... 604/22 |
| 4,842,579 | 6/1989 | Shiber . |
| 4,917,085 | 4/1990 | Smith ........................... 606/159 |
| 4,957,482 | 9/1990 | Shiber ........................... 604/22 |
| 4,969,879 | 11/1990 | Lichte .......................... 604/283 |
| 4,990,134 | 2/1991 | Auth . |
| 5,002,553 | 3/1991 | Shiber ........................... 606/159 |
| 5,019,089 | 5/1991 | Farr ............................. 606/172 |
| 5,030,201 | 7/1991 | Palestrant ..................... 604/22 |
| 5,085,662 | 2/1992 | Willard . |
| 5,112,345 | 5/1992 | Farr . |
| 5,135,483 | 8/1992 | Wagner et al. ............... 604/22 |
| 5,171,214 | 12/1992 | Kolber et al. ................ 604/82 |
| 5,217,474 | 6/1993 | Zacca et al. ................. 606/159 |
| 5,226,909 | 7/1993 | Evans et al. . |
| 5,242,460 | 9/1993 | Klein et al. . |
| 5,269,793 | 12/1993 | Simpson . |
| 5,286,253 | 2/1994 | Fucci ............................ 606/180 |
| 5,308,354 | 5/1994 | Zacca et al. . |
| 5,312,427 | 5/1994 | Shturman . |
| 5,314,407 | 5/1994 | Auth et al. . |
| 5,372,602 | 12/1994 | Burke ........................... 606/180 |
| 5,393,101 | 2/1995 | Matkovich ................... 285/3 |
| 5,417,672 | 5/1995 | Nita et al. ................... 606/169 |

FOREIGN PATENT DOCUMENTS

| | | |
|---|---|---|
| 0 117 519 A1 | 9/1984 | European Pat. Off. . |
| 35 19 626 A1 | 12/1986 | Germany . |
| 43 34 266 A1 | 4/1994 | Germany . |
| 2 044 103 | 10/1980 | United Kingdom . |

*Primary Examiner*—Michael Buiz
*Assistant Examiner*—Kevin Truong
*Attorney, Agent, or Firm*—Robert E. Atkinson

[57] ABSTRACT

The present invention provides for an improved rotating mechanical, or rotational, ablation device wherein one or more diamond plated burrs are attached to a driveshaft, which rotates at high speed driven by an advancer/turbine assembly. The driveshaft is provided with a quick connection/disconnection feature allowing for the easy removal of the burr/driveshaft assembly portion of the device from the advancer turbine assembly portion of the device.

16 Claims, 9 Drawing Sheets

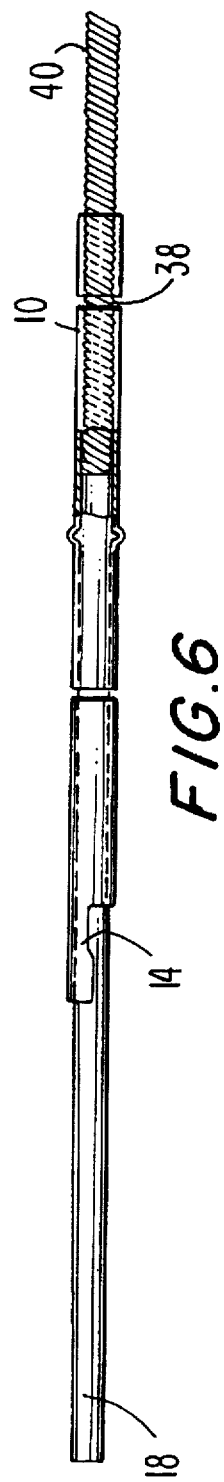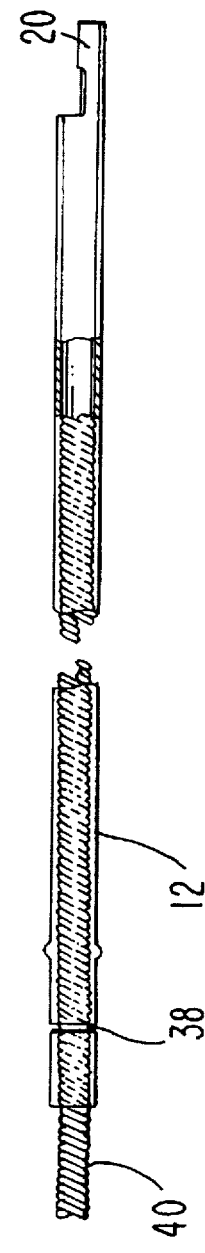

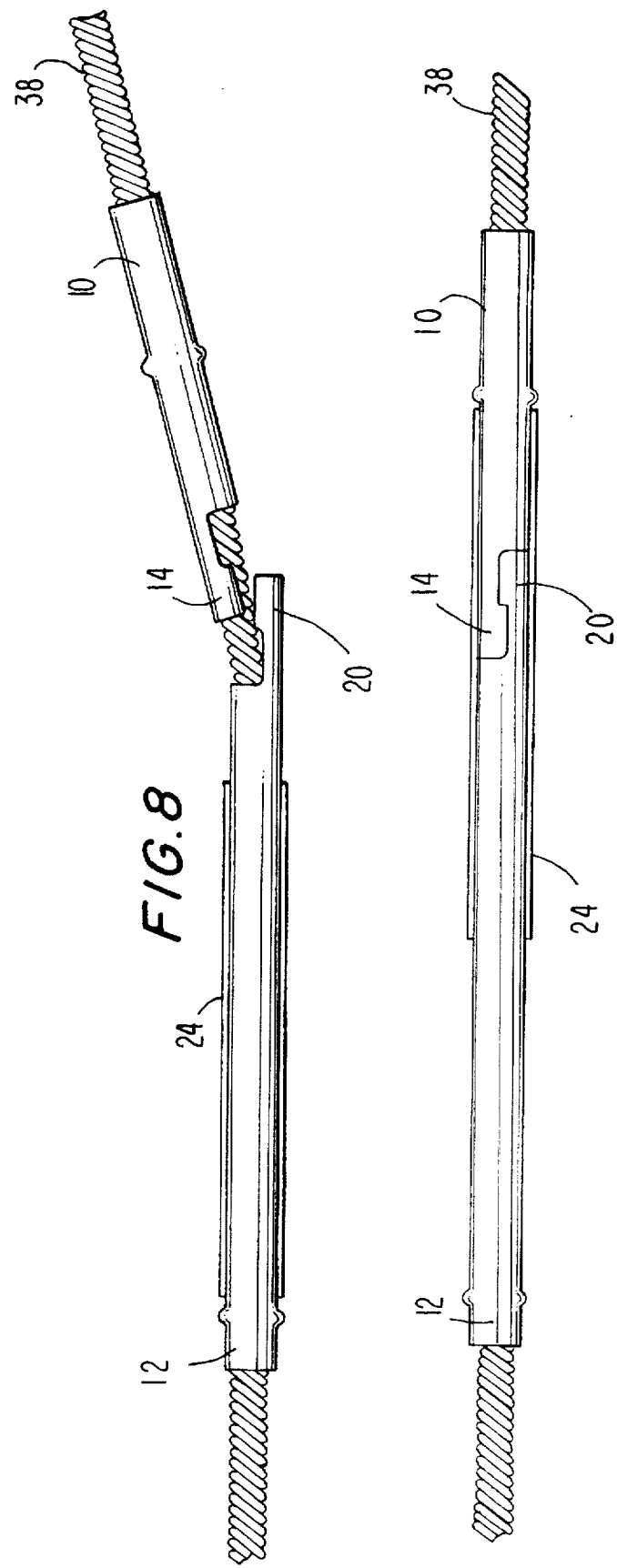

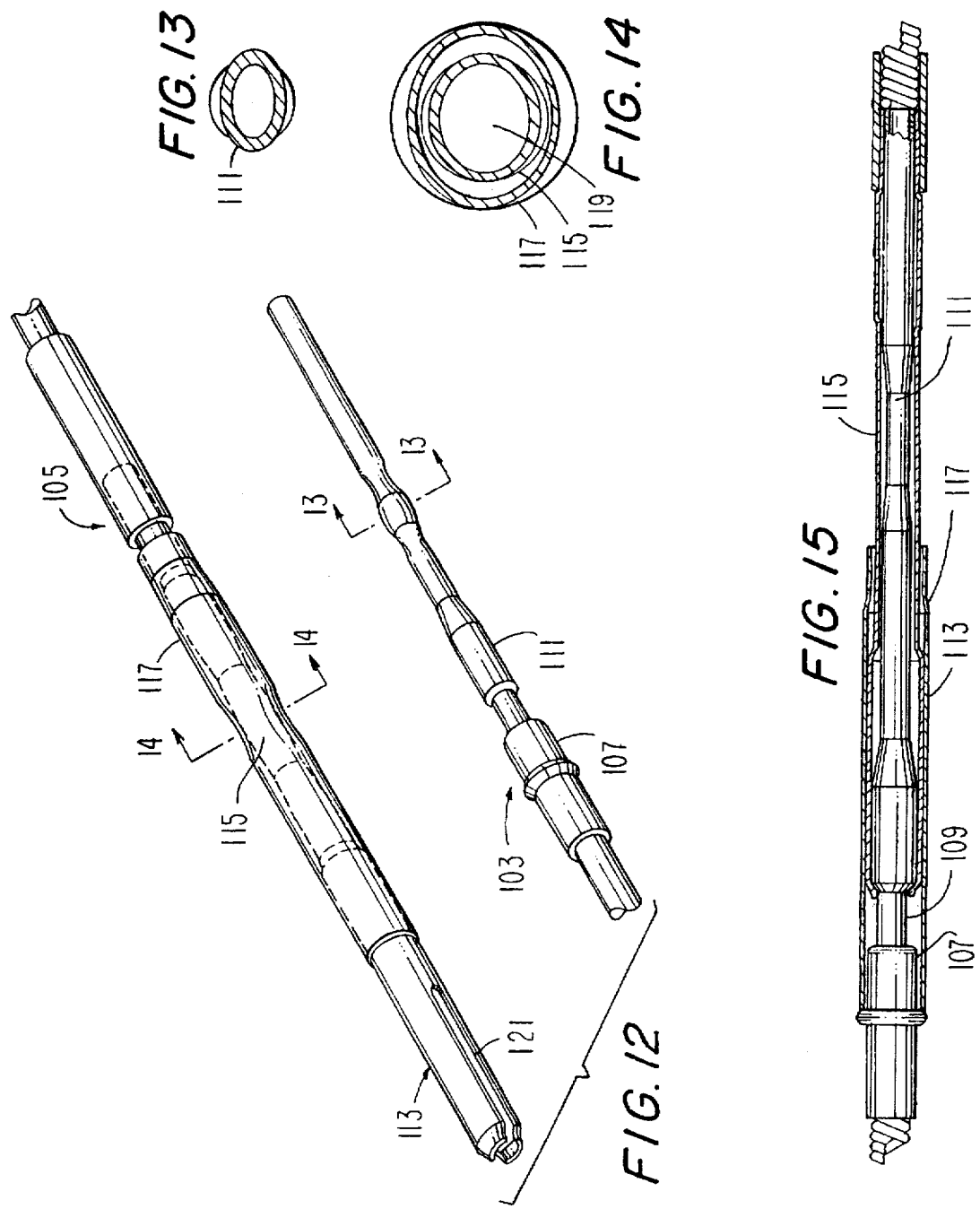

CONNECTABLE DRIVESHAFT SYSTEM

FIELD OF THE INVENTION

This invention relates to mechanical devices useful to remove abnormal deposits from within a patient's vessels. More particularly, this invention relates to a system for removably connecting the driveshafts for such mechanical devices.

BACKGROUND OF THE INVENTION

Various medical devices are known for removing abnormal deposits from corporal channels. For example, U.S. Pat. No. 4,990,134 entitled TRANSLUMINAL MICRODISSECTION DEVICE, and U.S. Pat. No. 4,445,509 entitled METHOD AND APPARATUS FOR REMOVAL OF ENCLOSED ABNORMAL DEPOSITS, describe a rotating mechanical system for removing plaque from an artery. U.S. Pat. No. 4,990,134 teaches the use of an ellipsoidal cutting head, or burr, coated with abrasive material such as tiny diamond chips. The cutting head rotates at such a tip velocity that the cutting head generates microscopic particles (on the order of 5 microns or less) and leaves behind a tissue base having a smooth appearance on the surface of the wall of the vessel from which an abnormal deposit has been removed.

Currently available rotating mechanical systems, such as that described above, have a permanent connection between the burr/driveshaft assembly and the advancer turbine assembly portions thereof, and each such system has a burr having one particular diameter, or size. Since more than one size burr is required in most atherectomy procedures, it is thus necessary to substitute a total system for each successive sized burr required. Also, such systems inherently involve the intimate interaction of the burr/driveshaft assembly portion of any rotating mechanical system with the patient's blood. Due to blood contamination and transmittal of disease considerations, and due to the complexity of the device, this precludes the ability to resterilize and reuse the device on more than one patient.

There is a definite need for a rotating mechanical device which is capable of allowing easy connection and disconnection between the burr/driveshaft assembly portion and the advancer turbine assembly portion to avoid the inherent necessity of having to dispose of the entire combined burr/driveshaft advancer turbine assembly each time a different burr is required on the same patient. Furthermore, general cost containment considerations also dictate the prudence and overall necessity of reducing the cost of each procedure which may be carried out utilizing any rotating mechanical device. The current invention addresses that mandate and provides a good and useful alternative to available rotating mechanical devices which can be used at lower overall cost on a per procedure basis.

SUMMARY OF THE INVENTION

The present invention represents an improved rotating mechanical device wherein burrs are attached to a driveshaft assembly which rotates at high speed, driven by an advancer turbine assembly. In the improvement provided for in the present invention, the aforementioned driveshaft assembly is provided with a quick connect/disconnect feature allowing for the easy removal of the burr/driveshaft assembly portion of the device from the advancer turbine assembly portion of the device, preferably at a point close to the advancer turbine assembly. This connect/disconnect point lies outside of the patient's body and beyond that portion of the burr/driveshaft assembly which normally comes in contact with a patient's body fluids.

More particularly, the improved device of the present invention provides for a connectable/disconnectable driveshaft featuring symmetrical mating interlocking teeth on both the proximal and distal portions of the connect/ disconnect joint. In one embodiment a close fitting tube is provided which slides over the inter-locking teeth to create a complete joint, which completely locked joint can be loaded in both the rotational and axial directions.

The parts making up the mechanism are formed from thinwalled tubing, creating a resultant joint that is both very small in diameter and also hollow. The novel hollow feature of the mated joint of the connectable driveshaft system of the present invention accommodates the necessary guidewire through the center of the connection, and the small diameter of the connection (e.g., about 0.045 inches O.D.) allows undisturbed flow of infusate around the outside of the connection.

An additional advantageous feature of the connection provided for according to the present invention is that it is extremely lightweight, and symmetrical, and thus has no significant impact on the inertial performance of the rotating mechanical device.

Also provided for use in conjunction with the connectable/disconnectable driveshaft of the present invention is a catheter which can itself be easily connected/ disconnected at the location of the driveshaft connection point by means of a Luer-type or similar fluid tight fitting. Disconnection of the catheter by this means allows easy access to the driveshaft connection/disconnection point.

The construction and obvious advantages of the present invention will best be understood from the following description of a specific embodiment when read in conjunction with the accompanying drawings.

BRIEF DESCRIPTION OF THE DRAWINGS

FIG. 6 is a detailed view of the proximal end of the connectable driveshaft system of the present invention showing the lock tooth and guide tube;

FIG. 7 is a detailed view of the distal end of the connectable driveshaft system of the present invention showing the distal lock tooth;

FIG. 8 is another view of an alternative embodiment of the connectable driveshaft system of the present invention showing the tube interlock in the disconnected position;

FIG. 9 is another view of an alternative embodiment of the present invention showing the interlock in the connected position and the slide tube in place;

FIG. 12 is an oblique, plan view of another embodiment of the invention;

FIG. 13 is a cross-sectional view along the line 13—13;

FIG. 14 is a cross-sectional view along the line 14—14; and

FIG. 15 is a cross-sectional longitudinal view of the embodiment of FIG. 12 in a locked position.

DETAILED DESCRIPTION OF THE INVENTION

Figure 1:
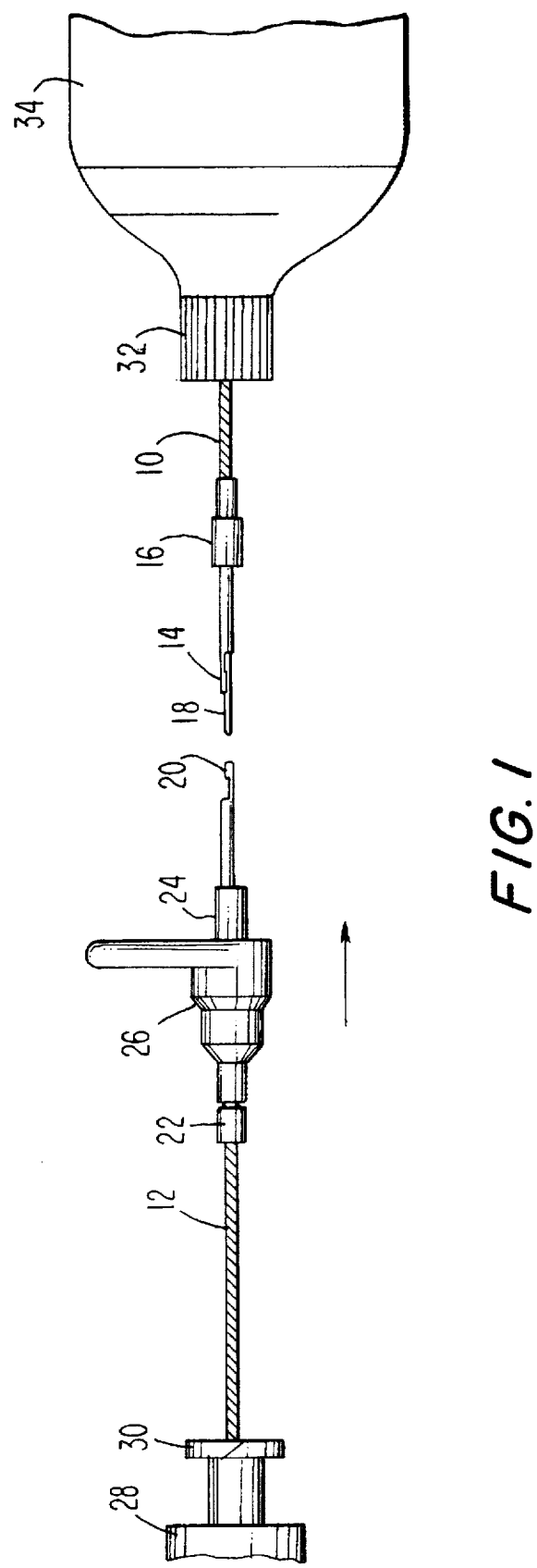
FIG. 1 is a view of the connectable driveshaft system of the present invention showing the various components in their disconnected position.

A preferred embodiment of the present invention shown in FIG. 1, comprises a driveshaft proximal section 10 and a distal section 12. The proximal section 10 is provided with a proximal lock tooth 14, a proximal stop 16 and a guide tube 18. The distal section is provided with a distal lock tooth 20, a distal stop 22 and a slide-lock tube 24, to which is removably attached a slide tube grip 26. The distal section 12 of the arrangement is also provided with a catheter sheath 28 having a Luer or similar type fitting 30 on the proximal end thereof, which fitting 28 mates with the companion fitting 32 located on the distal end of an advancer assembly 34. The fitting 32 concentrically encompasses the distal end of the proximal portion of the driveshaft proximal to proximal section 10, while catheter sheath 28 concentrically encompasses the portion of the driveshaft distal to distal section 12.

Figure 2:
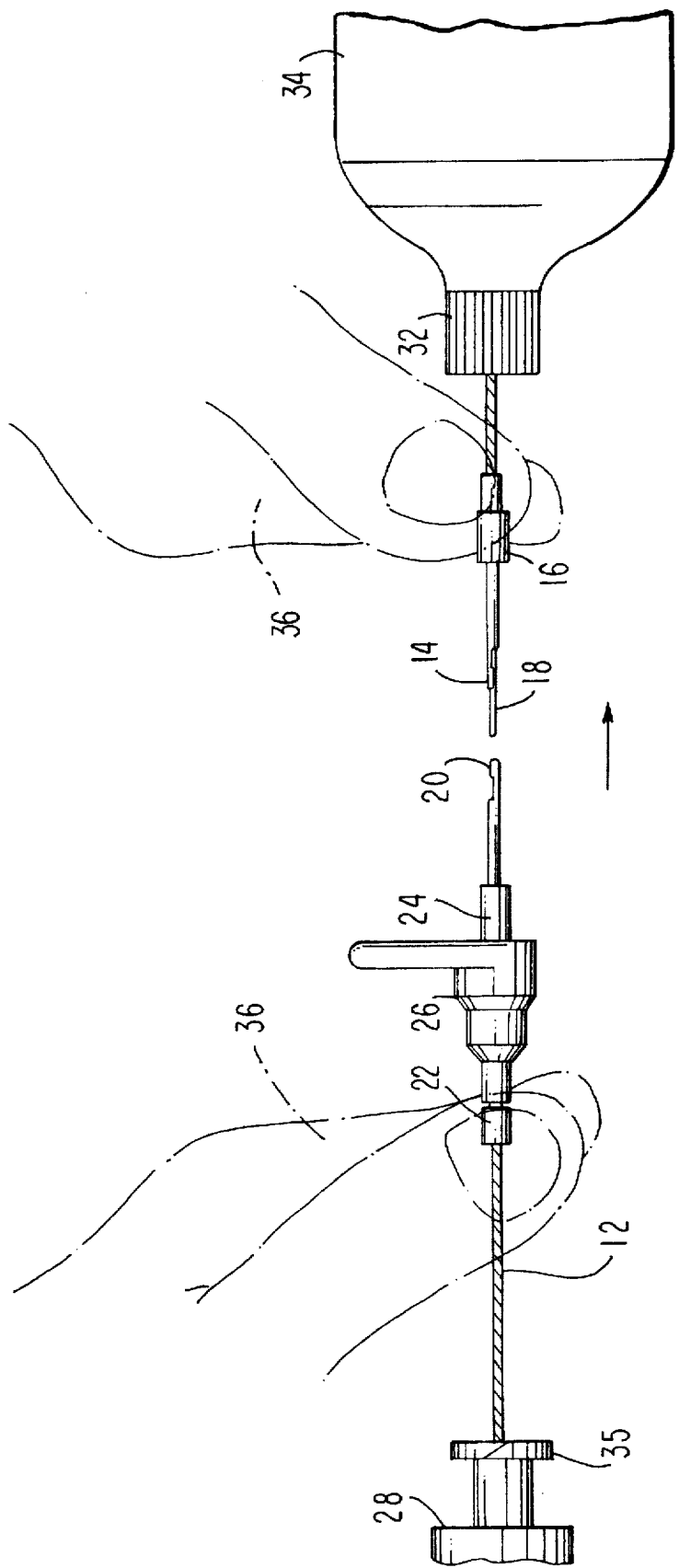
FIG. 2 is another view of the connectable driveshaft system of the present invention showing the distal and proximal shaft ends being manually connected.

In FIG. 2, the various components of the proximal end 10 and distal end 12 of the connectable driveshaft system of the present invention are again set forth with the relative position of the operator's fingers 36 being illustrated. The respective distal and proximal sections of the device shown in the disconnected position.

Figure 3:
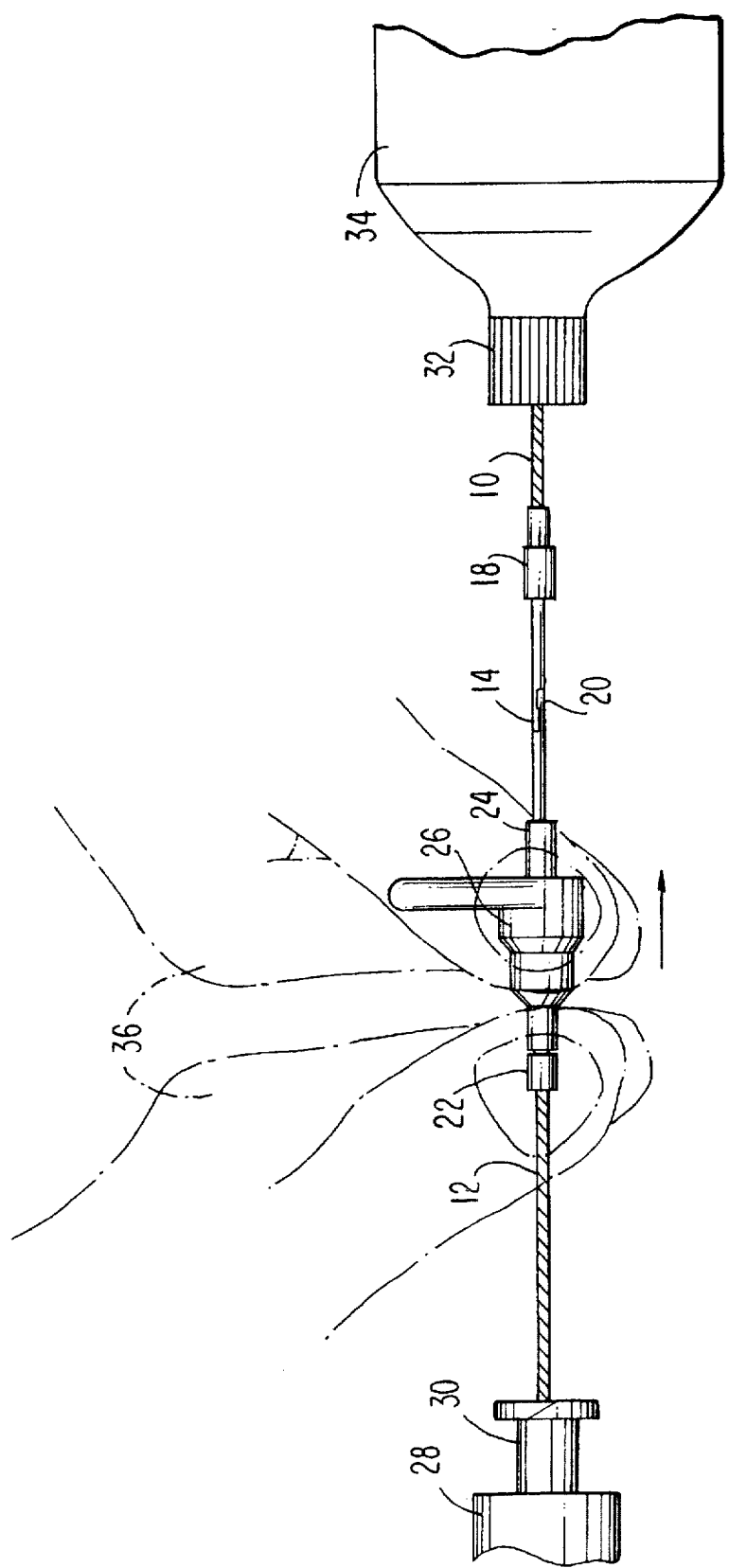
FIG. 3 is yet another view of the connectable driveshaft system of the present invention showing the two driveshaft ends in their connected position.

The respective proximal section 10 and distal section 12 of the disconnected driveshaft system of the present invention are shown in FIG. 3 with the respective guide tube 18 inserted into the distal end tip and the respective proximal lock tooth 14 engaged with the distal lock tooth 20. The device is shown in the connected position without the slide-lock tube 24 in the locked position. The respective operator's fingers 36 are shown grasping the distal end and the removable slide tube grip in preparation for sliding the slide-lock tube 24 proximally into the locked position over the engaged and mated proximal lock tooth 14 and distal lock tooth 20.

Figure 4:
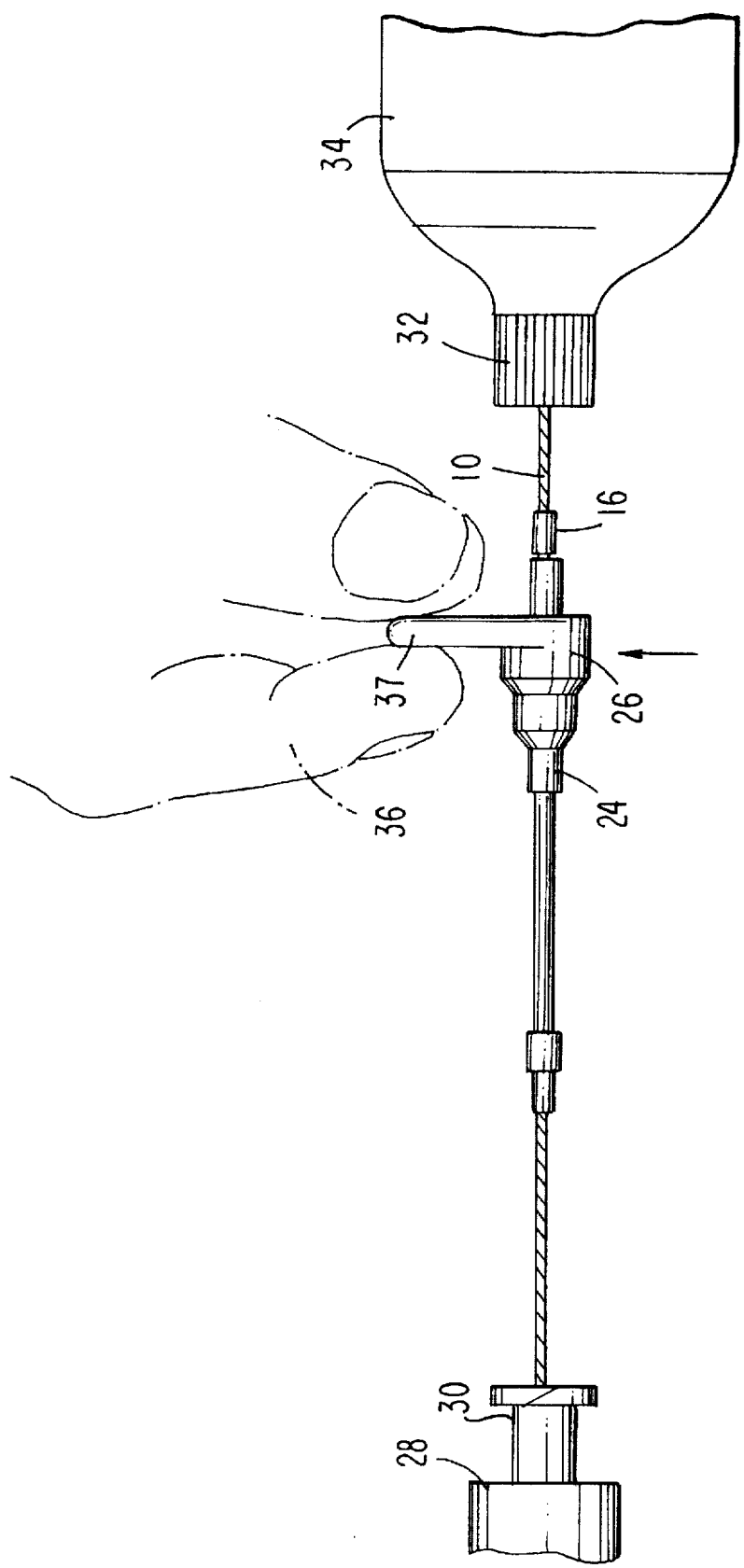
FIG. 4 is a view of the connected driveshaft of the present invention showing the positioning of the slide lock tube.

In FIG. 4 the disconnectable driveshaft system of the present invention is illustrated showing the proximal end 10 and the proximal stop 16, with the slide-lock tube 24 in the closed position and the fingers 36 of one of the operator's hands grasping the handle 37 of the removable slide tube grip 26 in preparation for removing same. Such removal would be done prior to connecting the catheter 28 Luer end 30 to the mating Luer end 32 on the advancer assembly 34.

Figure 5:
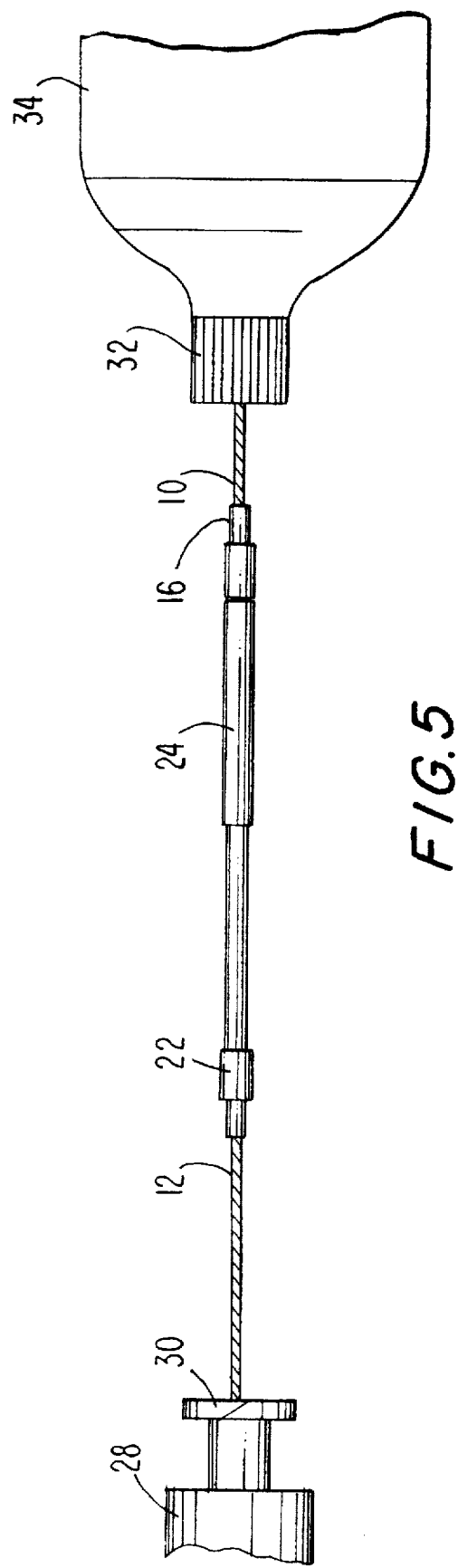
FIG. 5 is another view of the connected driveshaft system of the present invention showing the connected driveshaft with the slide lock tube in a closed position and the rubber slide tube grip removed.
Figure 11A:
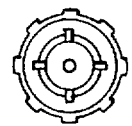
FIG. 11 is a plan view of the catheter proximal end shown in FIG. 13.

Slide tube grip 26 preferably has a peel-off feature, such as a slit (not shown), so it can be removed from the connected assembly. Once the tube grip 26 is removed, such as shown in FIG. 5, the disconnectable driveshaft system of the present invention can be seen where the proximal end 10 and the distal end 12 are connected the slide-lock tube 24 in the locked position resting against the proximal stop 16.

The disconnectable driveshaft system of the present invention can be disengaged by moving the slide-lock tube 24 distally toward the distal end 12 until slide-lock tube 24 touches stop 22. Then sections 14 and 20, as shown in FIG. 1, can be separated.

A detail of one embodiment of the proximal end 10 of the disconnectable driveshaft system of the present invention is shown in FIG. 6, with the guide tube 18, the proximal lock tooth 14 and the welded connection 38 between the proximal end 10 and the driveshaft 40 illustrated. Similarly, in FIG. 7, the distal end 12 of the disconnectable driveshaft system of the present invention is shown with the distal lock tooth 20, the laser weld connection 38 between the distal end 12 and the driveshaft 40 are illustrated.

FIGS. 8 and 9 are detailed views of an alternative embodiment of the connectable driveshaft system of the present invention which does not rely upon the use of a guide tube but rather shows the proximal end 10 and the distal end 12, the proximal lock tooth 14 engaged with the distal lock tooth 20 and the slide-lock tube 24 in the closed position. As illustrated further in FIG. 8, which represents a partially disconnected view of the alternative embodiment, the proximal end 10 relies upon the extension of the proximal driveshaft 40 through the proximal lock tooth 14 to be inserted into the distal end 12 prior to engagement with the distal lock tooth 20. In this view the slide-lock tube 24 is shown in the open position. FIG. 9 shows the same arrangement with the slide-lock tube 24 in the closed position.

Figure 10:
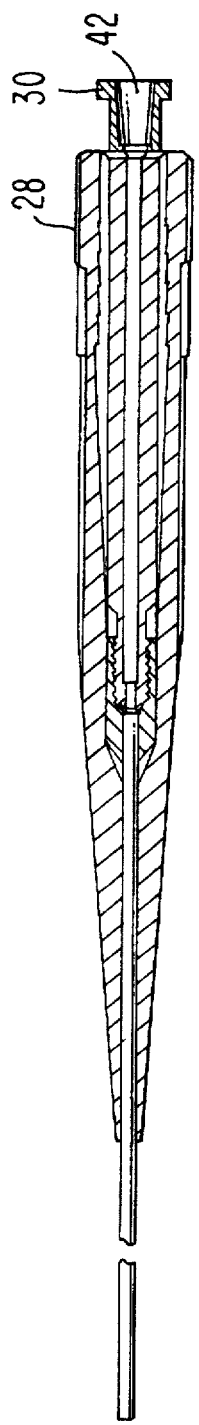
FIG. 10 is a detailed substantially cross-sectional view of one embodiment of the proximal end of a disconnectable catheter which may be used in conjunction with the disconnectable driveshaft system of the present invention.
Figure 11:

FIGS. 10 and 11 each show a detailed view of one embodiment of a disconnectable catheter end 28 showing the distal end of the Luer type fitting 30 and the distal end opening 42 for the admission of the driveshaft which extends through the body of the catheter 28.

Generally speaking, the overall dimensions of the preferred quick connect/disconnect joint of the present invention will be in the order of approximately two inches or less from end to end when the two mating interlocking teeth are joined and the slide-lock tube is slid into the locked position.

The overall outside diameter of the slide-lock tube utilized to lock the two mating interlocking teeth together will be about 0.045 inches O.D. and will generally be formed in such a manner as to provide a generally ovoid interior cross section over at least a portion of the said slide-lock tube so as to create a sufficient amount of interior friction between the interior walls of the slide-lock tube and the exterior walls of the joined interlocking teeth portion of the joint to prevent the slide-lock tube from moving unless sufficient force is applied to slide it into the unlocked position.

In the alternate embodiment of the slide-lock tube depicted in FIGS. 8 and 9, for example, the respective ends or center section of the slide-lock tube have been formed in such a manner as to render them slightly ovoid in crosssection, such that the ovoid end sections will have an O.D. in at least one dimension of approximately 0.035 inches.

FIGS. 12 to 15 detail another embodiment of the connector system according to the invention. This connector design is significant in that it connects completely together to a locked state in one smooth axial motion without the need for indexing for alignment of interlocking geometries.

Connector 101 comprises advancer side connector 103 and driveshaft side connector 105. Advance side connector 103 has a proximal portion 107 that connects to the advancer (not shown), recess 109, and male connector member 111. The distal portion of male connector 111 is oval, as is shown in the cross-section in FIG. 13. Driveshaft connector 105 comprises collet 113, distal portion 115, which is attached to the distally-extending driveshaft, and slide member 117. As shown in the cross-section in FIG. 14, distal portion 115 has an oval cross-section lumen 119 while slide member 117 has a substantially circular cross-section.

In the connected state shown in FIG. 15, torque is transmitted via the connector 101 by means of the oval cross-sectional tube 111 profile on the advancer side connector 103 which engages the oval cross-section lumen 119 on the driveshaft side. The non-uniform cross-sections prevent relative movement between tubes, therefore enabling the transmission of torque. These sections were constructed by placing a specific diameter mandrel inside the tubes to control geometry and squeezing down on the outside of the tube with micrometering until the controlling mandrel was engaged. The mandrel sizes for the prototypes were 0.0100" and 0.019" for the sections (13—13) and (14—14), respectively. One skilled in the art would appreciate that these dimensions can vary within useful ranges.

Axial retention is gained by means of the collet 113 geometry on the driveshaft side connector 105 engaging the recess 109 area on the advancer side connector 103. The collet 113 is flexible due to the slits 121 on either side of the collet 113, so that it can snap over the "Bullet" geometry of the male connector 111. It is then restrained from movement or locked in place by means of the slide tube 117 placed over the collet 113.

The slide tube geometry is such that it provides adequate friction on the driveshaft side connector, when in the "unlocked" position, to force the collet 113 over the "bullet" and into the recess area on the advancer side connector 103, before this friction is overcome to move the slide tube over the collet 113 into the "locked" position. This frictional effect is obtained by putting a slight squeeze on the slide tube in the same manner described previously. The mandrel diameter used for the slide tube was 0.030". Again, one skilled in the art would appreciate that this dimension can vary according to usage.

The materials of construction of the interlocking teeth and the close fitting slide-lock tube portions of the quick connect/disconnect means of the present invention will generally be constructed of appropriate physiologically acceptable metal such as stainless steel or other biocompatable materials. Stainless steel, such as 304 stainless steel, is particularly suitable.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

DIRECTORY

| No. | Element |
|-----|---------|
| 10 | driveshaft proximal section |
| 12 | driveshaft distal section |
| 14 | proximal lock tooth |
| 16 | proximal stop |
| 18 | guide tube |
| 20 | distal lock tooth |
| 22 | distal stop |
| 24 | slide-lock tooth |
| 26 | slide tube grip |
| 28 | catheter sheath |
| 30 | fluid tight fitting |
| 32 | reciprocal, companion fitting |

-continued
DIRECTORY

| No. | Element |
|-----|---------|
| 34 | advancer assembly |
| 36 | operator's finger(s) |
| 37 | handle |
| 38 | welded connection |
| 40 | driveshaft |
| 42 | distal opening |
| 101 | connector |
| 103 | advancer side connector |
| 105 | driveshaft connector |
| 107 | connector proximal portion |
| 109 | recess |
| 111 | male connector member |
| 113 | collet |
| 115 | connector member distal portion |
| 117 | slide member |
| 119 | connector member lumen |
| 121 | collet slit |

I claim:

1. In a rotating mechanical device capable of differentially cutting abnormal deposits from within a patient's vessels comprising a burr/driveshaft assembly connected to an advancer turbine assembly, the improvement comprising:

quick connect/disconnect means for connecting the burr/driveshaft assembly to the advancer turbine assembly, the quick connect/disconnect means includes a pair of symmetrical mating and interlocking teeth and a close fitting slide-lock tube, which slide-lock tube moves in such a manner as to permit it to slide over the mated interlocking teeth to form a complete joint which can be loaded in both the rotational and axial directions.

2. The rotating mechanical device of claim 1, wherein the symmetrical mating interlocking teeth which form the proximal and distal ends of the connectable/disconnectable joint are formed from thin walled tubing.

3. The rotating mechanical device of claim 2, wherein each of the mating interlocking portions which form the proximal and distal ends of the connectable/disconnectable joint are also provided with a stop means to limit the travel of the slide-lock tube.

4. The rotating mechanical device of claim 1, wherein the symmetrical mating interlocking teeth which form the quick connect/disconnect means are attached to the ends of the burr/driveshaft assembly portion of the device and the advancer turbine assembly portion of the device, respectively, by means of laser welds.

5. The rotating mechanical device of claim 1, wherein the slide-lock tube is provided with a removable slide tube grip to allow an operator to easily move the slide-lock tube into the locked position.

6. The rotating mechanical device of claim 1, wherein the distal end of the connectable/disconnectable driveshaft is also provided with a catheter surrounding the driveshaft, having at the end thereof a fluid tight type fitting, and the proximal end of the connectable/disconnectable drive is provided with a mating fluid tight type fitting which is located at the end of the advancer assembly and surrounds the proximal end of the driveshaft, such that when the two interlocking mating teeth are connected and the slide-lock tube placed in the locked position and after removal of the removable slide tube grip, the fluid tight fitting at the end of the catheter may be slid forward towards the end of the advancer turbine assembly and mated with the companion fluid tight fitting located at that point, thereby forming a continuous enclosure surrounding the entire driveshaft from the turbine assembly to the point where the burr/driveshaft assembly emerges from the end of the catheter inside the patient's body.

7. In a rotating mechanical device capable of differentially cutting abnormal deposits from within a patient's vessels comprising a burr/driveshaft assembly connected to a drive assembly, the improvement comprising:

quick connect/disconnect means for connecting the burr/driveshaft assembly to the drive assembly including a proximal member having proximal and distal sections, the proximal section being connected to the advancer and the distal section forming an elongate insertion member;

a distal member having proximal and distal sections, the proximal section having an opening and the distal section comprising a lumen in fluid communication with said opening; and lock means for retaining said insertion member within the opening, when the insertion member is received in the opening.

8. The rotating mechanical device of claim 7, wherein the proximal section of the distal member has at least one slit extending distally from said opening, and edges around said opening are received in the recess area of the proximal member.

9. The rotating mechanical device of claim 7, wherein the quick connect/disconnect means comprises a pair or reciprocating fitting ovoid members, the slide lock means being slidable over joined ovoid members to form a complete joint which can be loaded in both the rotational and axial directions.

10. The rotating mechanical device of claim 9, wherein the interlocking ovoid members which form the proximal and distal ends of the connectable/disconnectable joint are formed from thin walled tubing.

11. The rotating mechanical device of claim 9, wherein the symmetrical mating interlocking teeth which form the quick connect/disconnect means are attached to the ends of the burr/driveshaft assembly portion of the device and the drive assembly portion of the device, respectively, by means of laser welds.

12. The rotating mechanical device of claim 9, wherein the lock means is a slide-lock tube provided with a removable slide tube grip to allow an operator to easily move the slide-lock tube into the locked position.

13. The rotating mechanical device of claim 9, wherein each of the ovoid interlocking portions which form the proximal and distal ends of the connectable/disconnectable joint are also provided with a stop means to limit the travel of the slide-lock tube.

14. The rotating mechanical device of claim 9, wherein the distal end of the connectable/disconnectable driveshaft is also provided with a catheter surrounding the driveshaft having at the end thereof a fluid tight type fitting, and the proximal end of the connectable/disconnectable driveshaft is provided with a mating fluid tight type fitting which is located at the end of the advancer assembly and surrounds the proximal end of the driveshaft, such that when the two ovoid members are connected and the lock means is placed in the locked position and after removal of the removable slide tube grip, the fluid tight fitting at the end of the catheter may be slid forward towards the end of the drive assembly and mated with a companion fluid tight fitting located at that point, thereby forming a continuous enclosure surrounding the entire driveshaft from the drive assembly to the point where the burr/driveshaft assembly emerges from the end of the catheter inside the patient's body.

15. In a rotating mechanical device capable of differentially cutting abnormal deposits from within a patient's vessels comprising a burr/driveshaft assembly connected to a drive assembly, the improvement comprising:

quick connect/disconnect means for connecting the burr/driveshaft assembly to the drive assembly for rotation of the burr/driveshaft assembly, the quick connect/disconnect means providing a rigid connection which remains locked when rotated in either direction.

16. In a rotating mechanical device capable of differentially cutting abnormal deposits from within a patient's vessels comprising a burr/driveshaft assembly connected to a drive assembly, the improvement comprising:

quick connect/disconnect means for connecting the burr/driveshaft assembly to the drive assembly to rotate the burr/driveshaft assembly while the quick connect/disconnect means is disposed within a guide catheter.

* * * * *